(12) United States Patent
Watson et al.

(10) Patent No.: US 8,618,947 B2
(45) Date of Patent: Dec. 31, 2013

(54) DETECTING A SIGNAL QUALITY DECREASE IN A MEASUREMENT SYSTEM

(71) Applicant: Nellcor Puritan Bennett Ireland, Mervue (IE)

(72) Inventors: James Nicholas Watson, Dunfermline (GB); Paul Stanley Addison, Edinburgh (GB)

(73) Assignee: Nellcor Puritan Bennett Ireland, Mervue, Galway ( * ) Notice: Subject to any disclaimer, the term of this patent is extended or adjusted under 35 U.S.C. 154(b) by 0 days.

(21) Appl. No.: 13/854,026

(22) Filed: Mar. 29, 2013

(65) Prior Publication Data

US 2013/0229285 A1    Sep. 5, 2013

Related U.S. Application Data

(63) Continuation of application No. 12/242,204, filed on Sep. 30, 2008, now Pat. No. 8,410,951.

(51) Int. Cl.
*G08B 21/00* (2006.01)

(52) U.S. Cl.
USPC ..................................... 340/657; 375/240.19

(58) Field of Classification Search
USPC ............ 340/657; 702/69, 71, 72; 375/240.18, 375/240.19
See application file for complete search history.

(56) References Cited

U.S. PATENT DOCUMENTS

| | | |
|---|---|---|
| 4,289,141 A | 9/1981 | Cormier |
| 5,319,355 A | 6/1994 | Russek |
| 5,353,799 A | 10/1994 | Chance |
| 5,439,483 A | 8/1995 | Duong-Van |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod et al. |
| 5,827,195 A | 10/1998 | Lander |
| 5,846,190 A | 12/1998 | Woehrle |
| 5,967,995 A | 10/1999 | Shusterman et al. |
| 6,002,952 A | 12/1999 | Diab et al. |

(Continued)

FOREIGN PATENT DOCUMENTS

| | | |
|---|---|---|
| EP | 0913121 | 5/1999 |
| JP | 09-084776 | 3/1997 |

(Continued)

OTHER PUBLICATIONS

Addison, Paul S., The Illustrated Wavelet Transform Handbook, Taylor & Francis Group, 2002, 353 pages.

(Continued)

*Primary Examiner* — Toan N Pham

(57) ABSTRACT

Techniques for detecting a signal quality decrease are disclosed. A sensor or probe may be used to obtain a plethysmograph or photoplethysmograph (PPG) signal from a subject. A wavelet transform of the signal may be performed and a scalogram may be generated based at least in part on the wavelet transform. One or more characteristics of the scalogram may be determined. The determined characteristics may include, for example, energy values and energy structural characteristics in a pulse band, a mains hum band, and/or a noise band. Such characteristics may be analyzed to produce signal quality values and associated signal quality trends. One or more signal quality values and signal quality trends may be used to determine if a signal quality decrease has occurred or is likely to occur.

20 Claims, 17 Drawing Sheets
(2 of 17 Drawing Sheet(s) Filed in Color)

(56) References Cited

U.S. PATENT DOCUMENTS

| | | | |
|---|---|---|---|
| 6,036,653 A | 3/2000 | Baba et al. |
| 6,094,592 A | 7/2000 | Yorkey et al. |
| 6,095,984 A | 8/2000 | Amano et al. |
| 6,117,075 A | 9/2000 | Barnea |
| 6,129,675 A | 10/2000 | Jay |
| 6,135,966 A | 10/2000 | Ko |
| 6,171,257 B1 | 1/2001 | Weil et al. |
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,325,761 B1 | 12/2001 | Jay |
| 6,360,114 B1 | 3/2002 | Diab et al. |
| 6,361,501 B1 | 3/2002 | Amano et al. |
| 6,393,311 B1 | 5/2002 | Edgar, Jr. et al. |
| 6,449,501 B1 | 9/2002 | Reuss |
| 6,510,329 B2 | 1/2003 | Heckel |
| 6,561,986 B2 | 5/2003 | Baura et al. |
| 6,606,510 B2 | 8/2003 | Swedlow et al. |
| 6,606,511 B1 | 8/2003 | Ali et al. |
| 6,608,934 B2 | 8/2003 | Scheirer |
| 6,650,917 B2 | 11/2003 | Diab et al. |
| 6,654,623 B1 | 11/2003 | Kastle |
| 6,654,624 B2 | 11/2003 | Diab et al. |
| 6,675,031 B1 | 1/2004 | Porges et al. |
| 6,699,194 B1 | 3/2004 | Diab et al. |
| 6,745,060 B2 | 6/2004 | Diab et al. |
| 6,771,994 B2 | 8/2004 | Kiani et al. |
| 6,810,277 B2 | 10/2004 | Edgar, Jr. et al. |
| 6,822,564 B2 | 11/2004 | Al-Ali |
| 6,826,419 B2 | 11/2004 | Diab et al. |
| 6,898,452 B2 | 5/2005 | Al-Ali et al. |
| 6,931,269 B2 | 8/2005 | Terry |
| 6,970,792 B1 | 11/2005 | Diab |
| 6,987,994 B1 | 1/2006 | Mortz |
| 6,993,377 B2 | 1/2006 | Flick et al. |
| 7,001,337 B2 | 2/2006 | Dekker |
| 7,006,856 B2 | 2/2006 | Baker, Jr. et al. |
| 7,020,507 B2 | 3/2006 | Scharf |
| 7,024,233 B2 | 4/2006 | Ali et al. |
| 7,035,679 B2 | 4/2006 | Addison |
| 7,043,293 B1 | 5/2006 | Baura |
| 7,054,453 B2 | 5/2006 | Causevic |
| 7,054,454 B2 | 5/2006 | Causevic et al. |
| 7,079,888 B2 | 7/2006 | Oung et al. |
| 7,171,269 B1 | 1/2007 | Addison |
| 7,173,525 B2 | 2/2007 | Albert |
| 7,194,293 B2 | 3/2007 | Baker, Jr. |
| 7,203,267 B2 | 4/2007 | De Man et al. |
| 7,225,013 B2 | 5/2007 | Geva et al. |
| 7,254,500 B2 | 8/2007 | Makeig |
| 7,289,835 B2 | 10/2007 | Mansfield |
| 7,355,512 B1 | 4/2008 | Al-Ali |
| 7,457,652 B2 | 11/2008 | Porges et al. |
| 7,471,969 B2 | 12/2008 | Diab et al. |
| 7,477,571 B2 | 1/2009 | Melese et al. |
| 7,499,835 B2 | 3/2009 | Weber et al. |
| 7,515,949 B2 | 4/2009 | Norris |
| 7,519,488 B2 | 4/2009 | Fu et al. |
| 7,523,011 B2 | 4/2009 | Akiyama et al. |
| 7,566,306 B2 | 7/2009 | Fujiwara et al. |
| 8,370,080 B2 | 2/2013 | Watson et al. |
| 2003/0225337 A1 | 12/2003 | Scharf |
| 2005/0043616 A1 | 2/2005 | Chinchoy |
| 2006/0122476 A1 | 6/2006 | Van Slyke |
| 2006/0211930 A1 | 9/2006 | Scharf et al. |
| 2006/0220881 A1 | 10/2006 | Al-Ali et al. |
| 2006/0226992 A1 | 10/2006 | Al-Ali et al. |
| 2006/0238358 A1 | 10/2006 | Al-Ali et al. |
| 2006/0258921 A1 | 11/2006 | Addison et al. |
| 2006/0265022 A1 | 11/2006 | John et al. |
| 2007/0021673 A1 | 1/2007 | Arbel et al. |
| 2007/0043269 A1 | 2/2007 | Mannheimer et al. |
| 2007/0073120 A1 | 3/2007 | Li et al. |
| 2007/0073124 A1 | 3/2007 | Li et al. |
| 2007/0167694 A1 | 7/2007 | Causevic et al. |
| 2007/0167851 A1 | 7/2007 | Vitali et al. |
| 2007/0208259 A1 | 9/2007 | Mannheimer |
| 2007/0282212 A1 | 12/2007 | Sierra et al. |
| 2008/0039699 A1 | 2/2008 | Neumann |
| 2008/0045832 A1 | 2/2008 | McGrath |
| 2008/0081971 A1 | 4/2008 | Ollerdessen |
| 2008/0082018 A1 | 4/2008 | Sackner et al. |
| 2008/0091092 A1 | 4/2008 | Al-Ali |
| 2008/0091093 A1 | 4/2008 | Al-Ali |
| 2008/0214903 A1 | 9/2008 | Orbach |
| 2008/0221418 A1 | 9/2008 | Al-Ali et al. |
| 2008/0242955 A1 | 10/2008 | Uutela et al. |
| 2008/0243021 A1 | 10/2008 | Causevic et al. |
| 2010/0016691 A1 | 1/2010 | Watson et al. |
| 2010/0081898 A1 | 4/2010 | Addison et al. |

FOREIGN PATENT DOCUMENTS

| | | |
|---|---|---|
| WO | WO 01/25802 | 4/2001 |
| WO | WO 01/62152 | 8/2001 |
| WO | WO 03/055395 | 7/2003 |
| WO | WO 2004/075746 | 9/2004 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006, 4 pages.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

International Search Report PCT/IB2009/006898, 4 pages, mailed on Jan. 2, 2010.

DETECTING A SIGNAL QUALITY DECREASE IN A MEASUREMENT SYSTEM

This application is a continuation of U.S. patent application Ser. No. 12/242,204 filed on Sep. 30, 2008, which is incorporated by reference herein in its entirety.

SUMMARY

The present disclosure relates to signal processing and, more particularly, the present disclosure relates to using characteristics of one or more wavelet scalograms of a signal, such as a photoplethysmograph (PPG) signal, to determine if a signal quality decrease has occurred or is likely to occur in a system, such as a pulse oximetry system.

In an embodiment, a pulse oximetry system is used to measure and analyze physiological characteristics of a patient. A signal quality decrease may occur when the target stimulus (e.g., a patient fingertip, toe, forehead, earlobe, or foot) is no longer adequately reflected in measurement of the PPG signal. Possible causes of such a signal quality decrease include motion artifacts that may be caused by, for example, voluntary or involuntary respiration, eye movements, swallowing, yawning, cardiac motion, and/or general body movement of a patient, the sensor being accidentally dislodged, or the sensor or any constituent component of the sensor being damaged or otherwise malfunctioning.

In an embodiment, a PPG signal is transformed using a continuous wavelet transform. Continuous wavelet transforms allow for the use of multiple wavelets that are each scaled in accordance with scales of interest of a signal such that smaller scale components of a signal are transformed using wavelets scaled more compactly than wavelets used to extract larger scale components of the signal. The window size of data to which each wavelet gets applied varies according to scale as well. Thus, a higher resolution transform is possible using continuous wavelets relative to discrete techniques.

In an embodiment, one or more scalograms may be obtained by processing the wavelet transform. Each scalogram may represent the energy density of the PPG signal, where a suitable scaling has been performed to emphasize certain scale values or ranges of interest for the analysis of the PPG signal. In addition, the scalogram may contain information on the real part of the wavelet transform, the imaginary part of the wavelet transform, the phase of the wavelet transform, any other suitable part of the wavelet transform, or any combination thereof.

In an embodiment, a set of one or more characteristics may be determined by applying one or more time-windows to one or more scalograms of a PPG signal. Time-windows may be continuous or discontinuous, and may be used to isolate regions or scale bands of the one or more scalograms. The characteristics that are determined may chosen based on a pre-existing knowledge of features that are expected in a scalogram before and after a signal quality decrease event. For example, the characteristics that are determined may include some or all of the following items: energy levels in a pulse band, energy levels in a mains hum band; energy levels in a noise band, energy structure in the pulse band, energy structure in the mains hum band, and energy structure in the noise band.

In an embodiment, a set of one or more characteristics derived from one or more scalograms may be analyzed. An analysis may include curve-fitting one or more plots of data related to the one or more characteristics. Plots of data may depict the average or maximum energy observed in a given region of the scalogram as a function of time, and curve-fitting may involve interpolating or least-squares fitting the plotted data. An analysis may include calculating one or more signal-to-noise levels based on the data related to the one or more characteristics. The signal-to-noise levels may correspond to the ratio of average or maximm energy density in a suitable signal band, such as the pulse band, to the average or maximum energy density in a suitable non-signal band, such as the mains hum band or the noise band.

In an embodiment, one or more signal qualities and one or more associated signal quality trends may be determined based on an analysis of characteristics derived from one or more scalograms. Each signal quality value may be represented by a number from 0 to 100, where a larger number indicates a higher quality signal, and each signal quality trend may be represented by a number representing a rate of increase or a rate of decrease in the signal quality value versus time. One or more signal qualities and one or more associated signal quality trends may be combined or weighed according to any suitable method to determine an overall signal quality value and an associated overall signal quality trend value.

In an embodiment, an overall signal quality value and an associated overall signal quality trend value may be used to determine or anticipate the presence of a signal quality value decrease event. A signal may be triggered if it is determined that a signal quality decrease event has occurred or that one is likely to occur. For example, the triggered signal may sound an alarm or display one or more on-screen messages to alert a user of the signal quality decrease. If it is determined that the signal quality decrease event has not occurred, then a new portion of a scalogram may be analyzed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features of the present disclosure, its nature and various advantages will be more apparent upon consideration of the following detailed description, taken in conjunction with the accompanying drawings in which.

DETAILED DESCRIPTION

Figure 1:
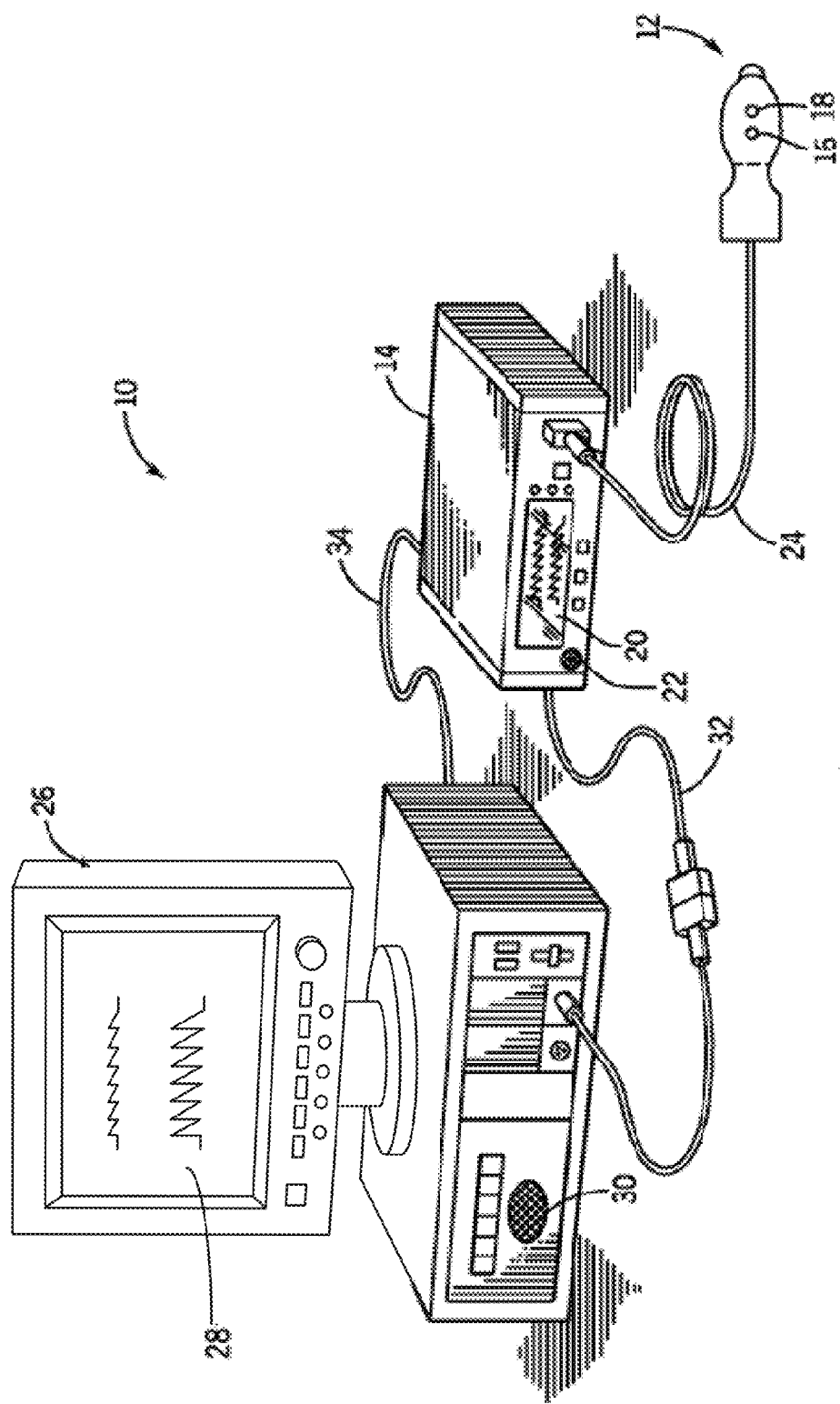
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:

$\lambda$=wavelength;

t=time;

I=intensity of light detected;

$I_o$=intensity of light transmitted;

s=oxygen saturation;

$\beta_o$, $\beta_r$=empirically derived absorption coefficients; and l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_0 + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR})-\beta_r(\lambda_{IR})) - \frac{d\log I(\lambda_{IR})}{dt}(\beta_o(\lambda_R)-\beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}}$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_{IR})}$$

$$= R \quad (7)$$

which defines a cluster of points whose slope of y versus x will give R where $$x(t) = [I(t_2,\lambda_{IR}) - I(t_1,\lambda_{IR})]I(t_1,\lambda_R)$$

$$y(t) = [I(t_2,\lambda_R) - I(t_1,\lambda_R)]I(t_1,\lambda_{IR})$$

$$y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
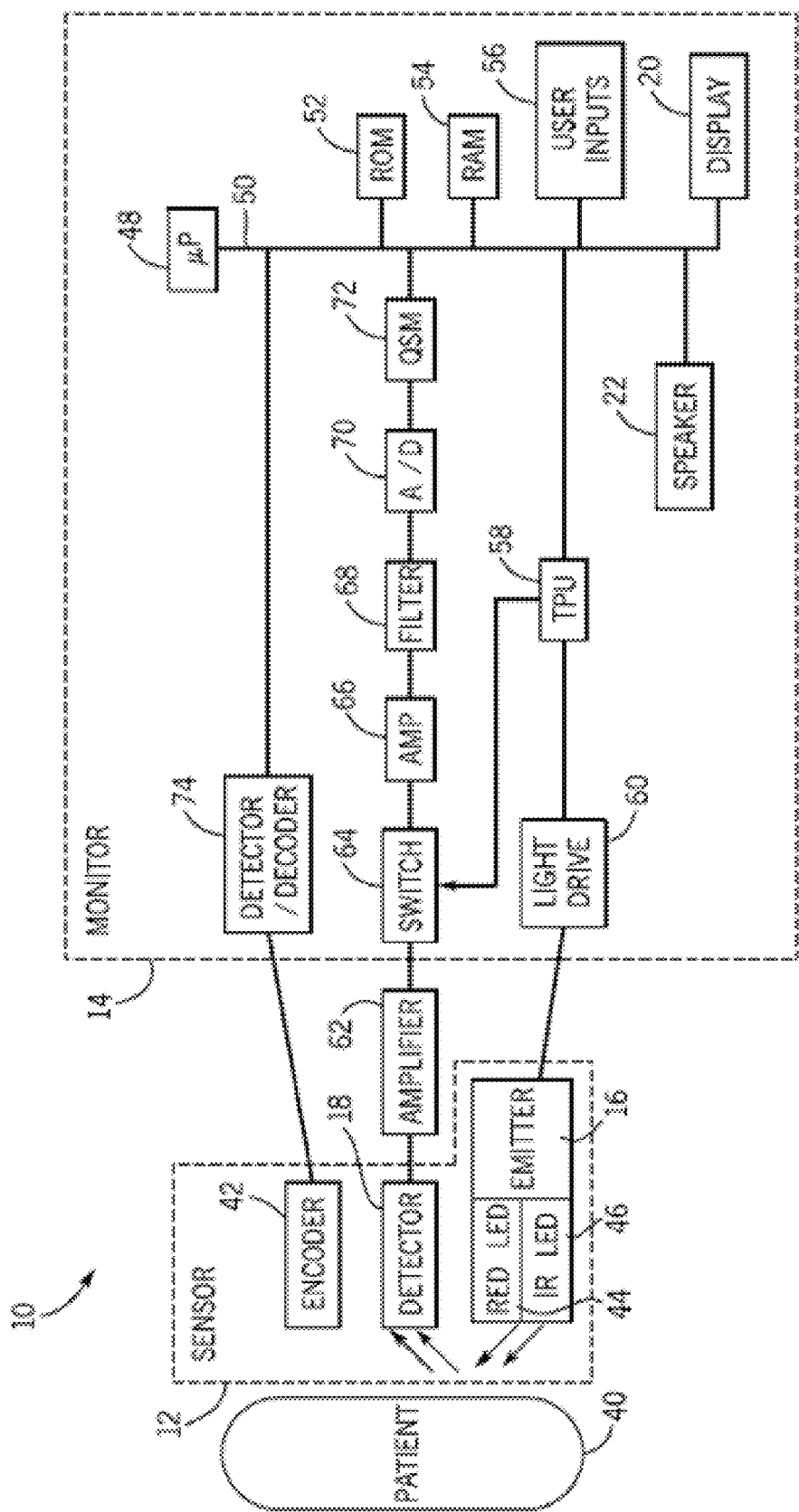
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40. An example of a device configured to perform such calculations is the Model N600x pulse oximeter available from Nellcor Puritan Bennett LLC.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise and motion artifacts, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Motion artifact can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \qquad (9)$$

where ψ*(t) is the complex conjugate of the wavelet function ψ(t), a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \qquad (10)$$

where '| |' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \qquad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \qquad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
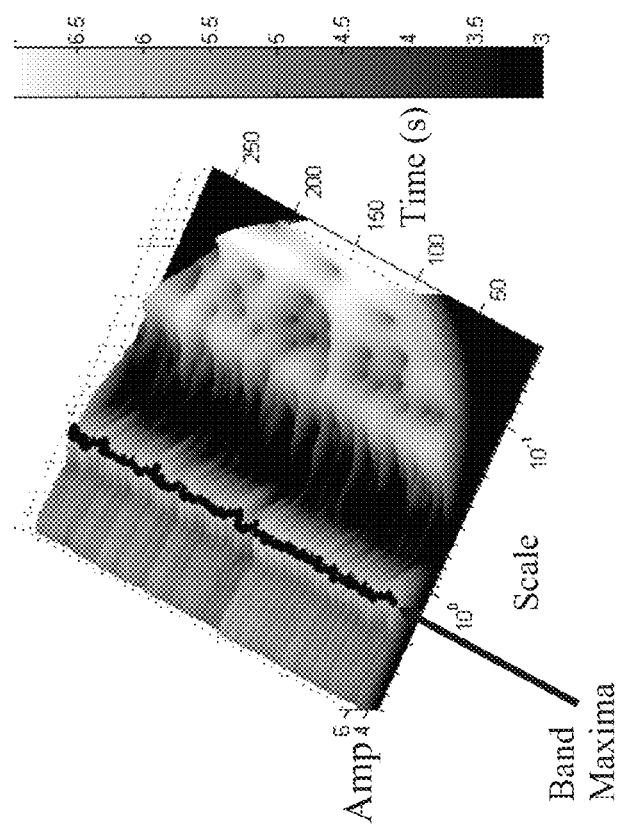
FIGS. 3(a) and 3(b) show illustrative views of a scalogram derived from a PPG signal in accordance with an embodiment.
Figure 3A:
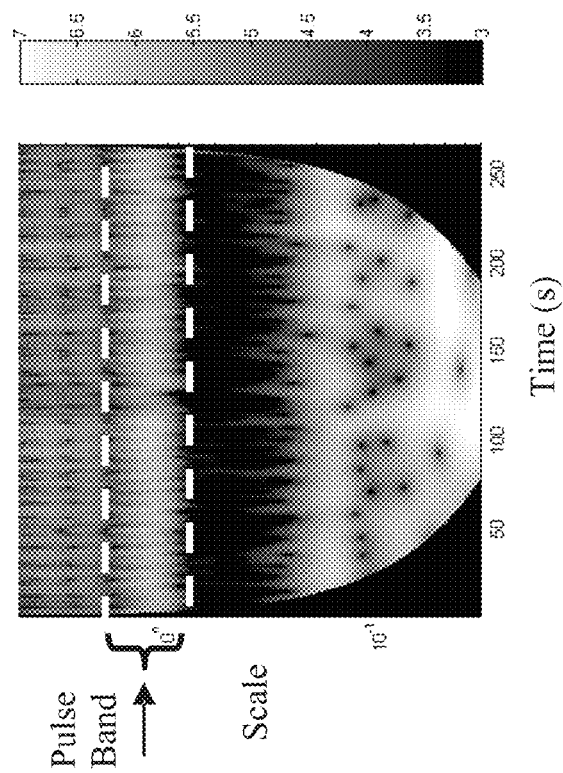

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
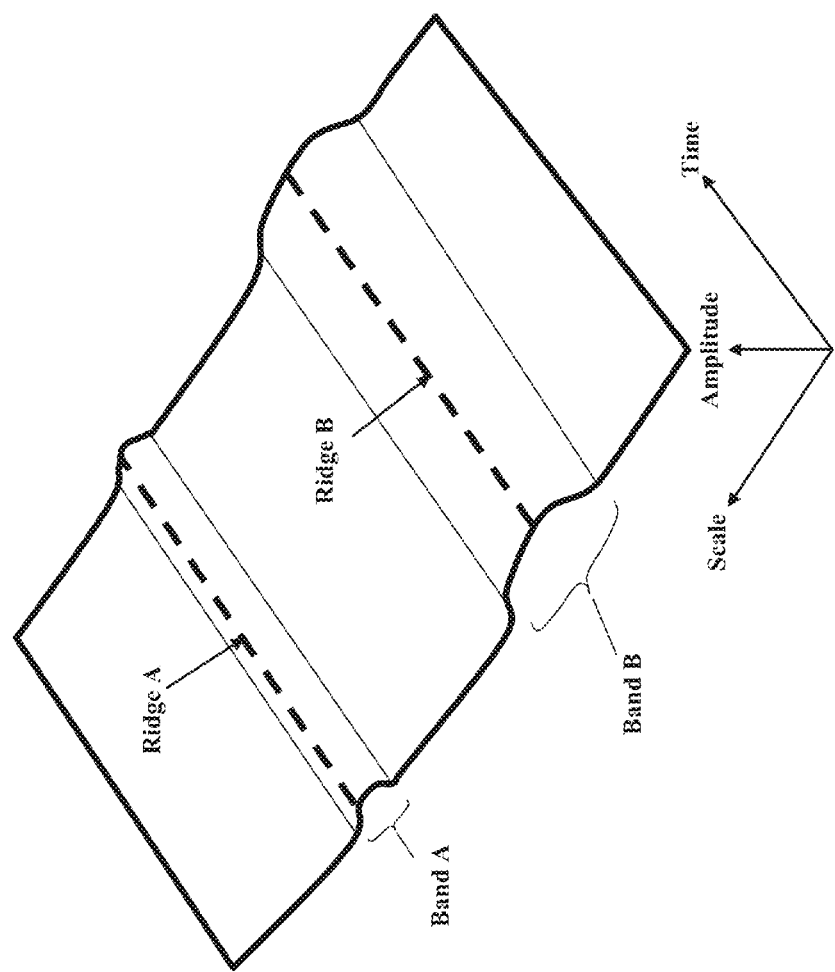
FIG. 3(c) shows an illustrative scalogram derived from a signal containing two pertinent components in accordance with an embodiment.
Figure 3D:
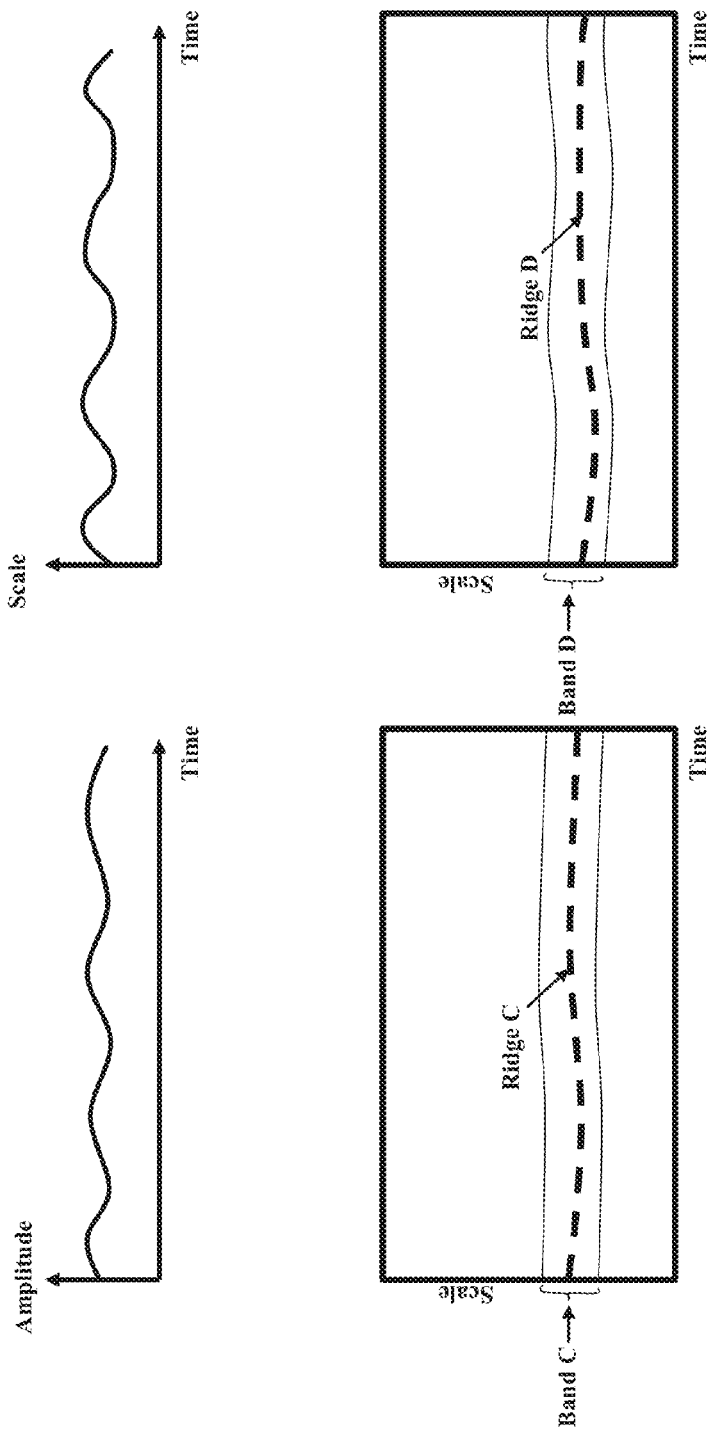
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In an embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a, b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a, b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
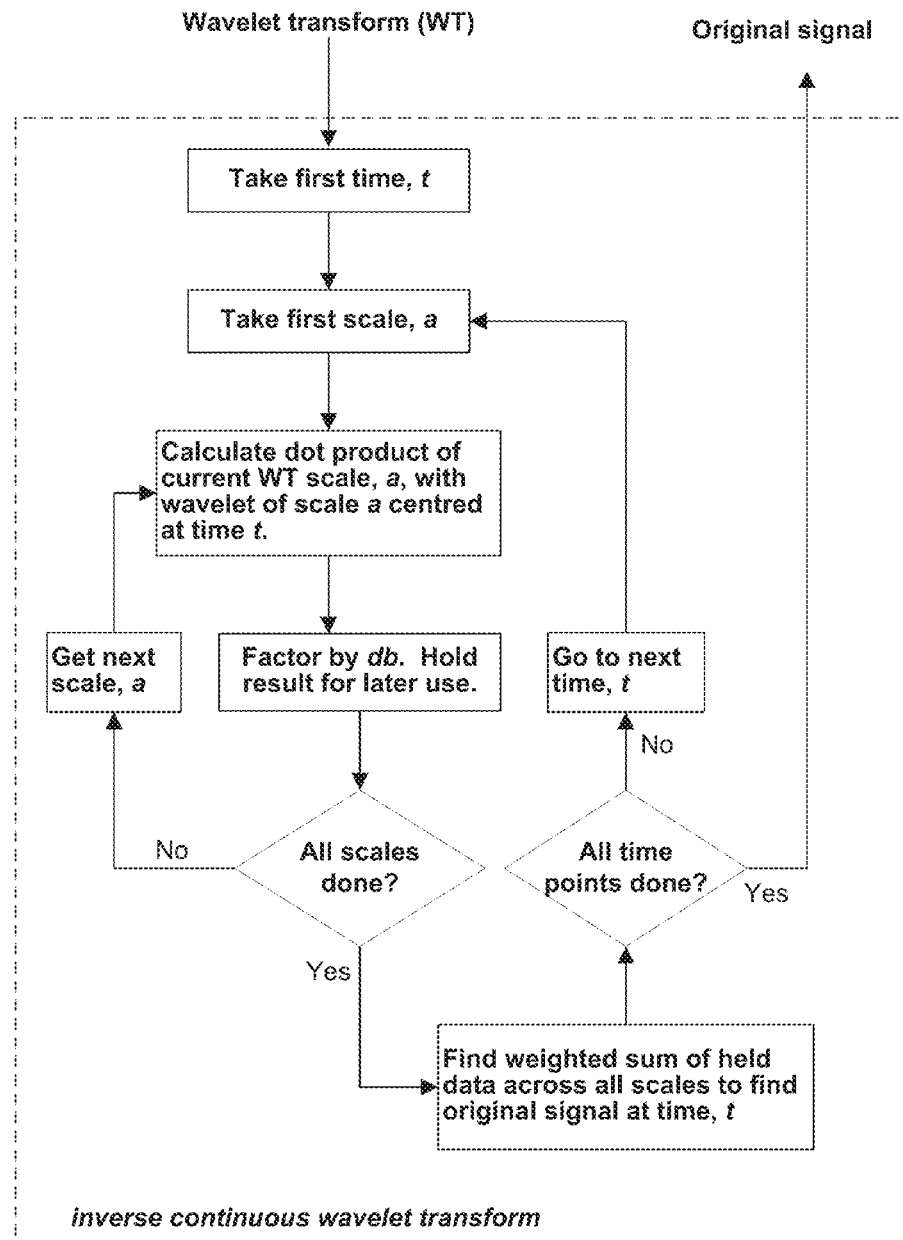
FIGS. 3(e) and 3(f) are flow charts of illustrative steps involved in performing an inverse continuous wavelet transform in accordance with embodiments.
Figure 3F:
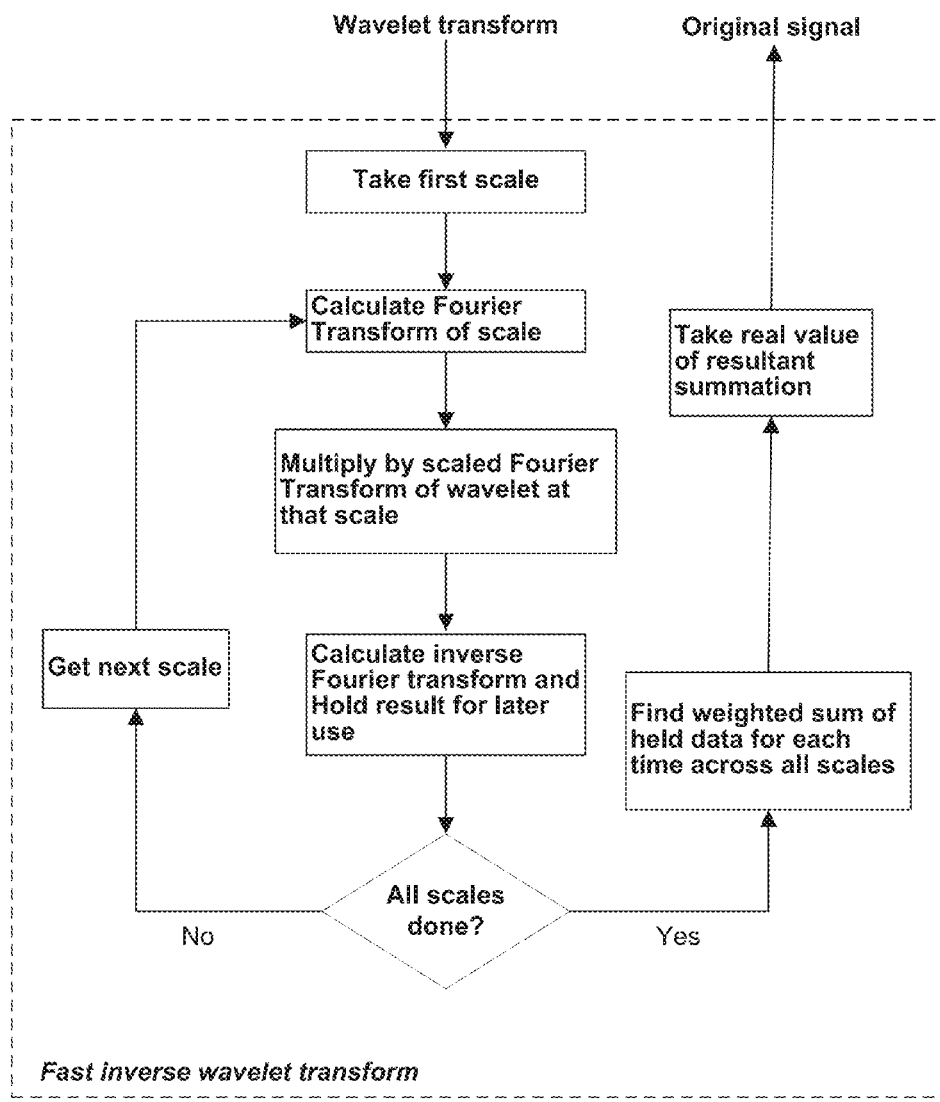

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
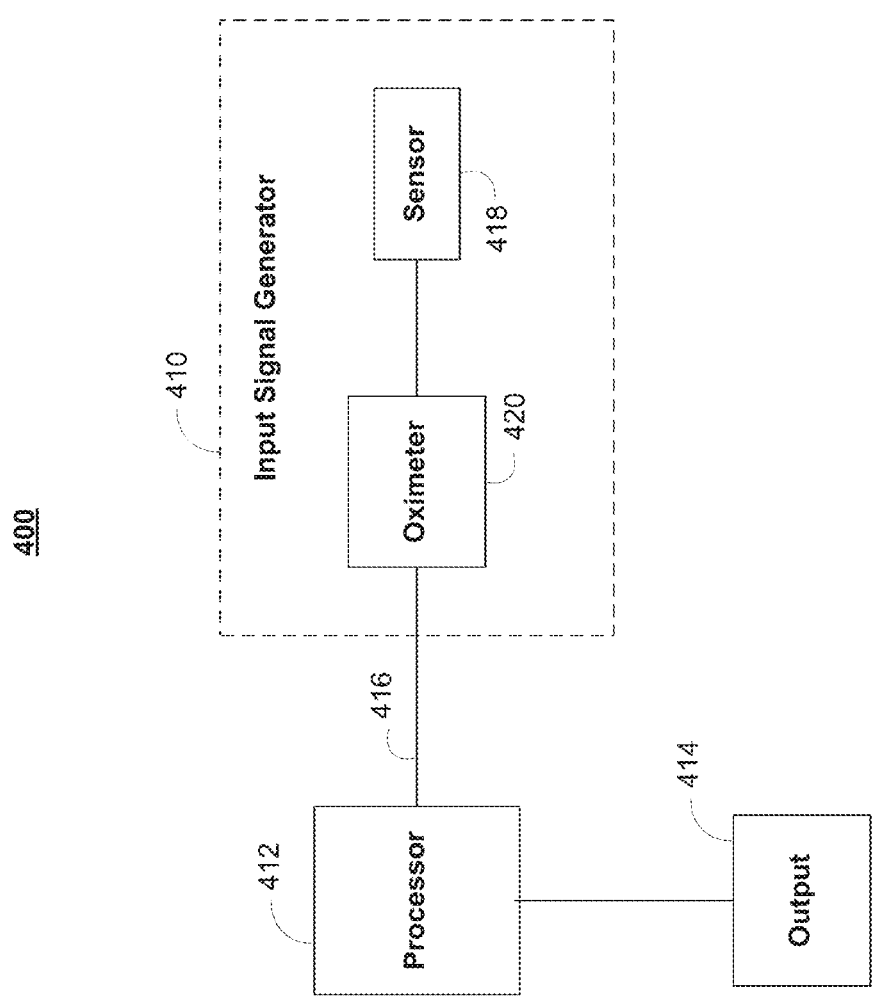
FIG. 4 is a block diagram of an illustrative continuous wavelet processing system in accordance with an embodiment.

FIG. 4 is an illustrative continuous wavelet processing system in accordance with an embodiment. In an embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In an embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
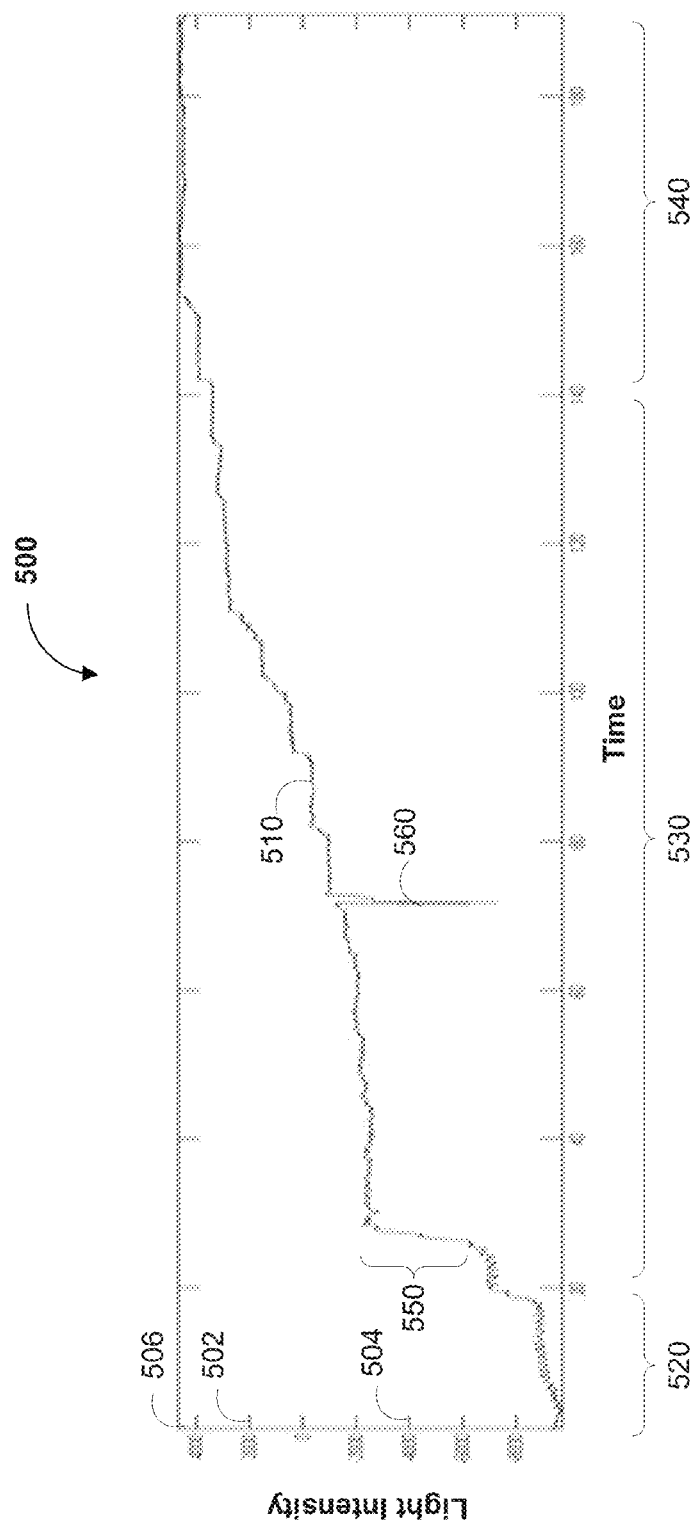
FIG. 5 shows an illustrative plot of a PPG signal taken during a period of decreasing signal quality in accordance with an embodiment.

FIG. 5 shows an illustrative plot of a PPG signal 510 taken during a period of decreasing signal quality in accordance with an embodiment. Plot 500 displays time on the x-axis and light intensity on the y-axis. The y-axis may represent the light intensity detected by detector 18 (FIG. 1) that emanates from the tissue of patient 40 (FIG. 1). Larger values on the y-axis indicate larger light intensity measurements than smaller values on the y-axis (for example, light intensity value 502 represents a larger light intensity than light intensity value 504). PPG signal 510 may be obtained, for example, from sensor 12 (FIG. 1) or from averaging or otherwise combining a plurality of signals derived from a suitable sensor array, as discussed in relation to FIG. 1. Plot 500 may be displayed using any suitable display device such as, for example, monitor 20 (FIG. 1), display 28 (FIG. 1), a PDA, a mobile phone, or any other suitable display device. Additionally, plot 500 may be displayed on multiple display devices, or it may not be displayed on any display devices.

A period of decreasing signal quality is a period in which the "quality" of the PPG signal 510 decreases in some way. The quality of PPG signal 510 may be determined using a system such as system 10 (FIGS. 1 and 2) and/or system 400 (FIG. 4) to perform a suitable analysis of the signal. For example, the quality of PPG signal 510 may be characterized by analyzing the energy of the signal or by calculating the signal-to-noise level of the signal. These characteristics may be calculated, for example, from a suitable scalogram of PPG signal 510, and in particular, may be calculated using one or more portions of such a scalogram.

A period of decreasing signal quality may indicate that the intended target stimulus (e.g., patient's 40 (FIG. 2) fingertip, toe, forehead, earlobe, or foot) is not being adequately measured by, for example, pulse oximetry system 10 (FIGS. 1 and 2). Possible causes of a period of decreasing signal quality may include: sensor 20 (FIG. 1) being slowly dislodged from patient 40 (FIG. 2), sensor 20 (FIG. 1) or any constituent component of the sensor 20 (FIG. 1) being damaged or otherwise malfunctioning, and/or a connecting cable (e.g., cable 24, 32, or 34 of FIG. 1) being gradually removed or otherwise malfunctioning. For example, PPG signal 510 was generated during an experiment in which the pulse oximeter probe was gradually loosened from the finger of patient 40 (FIG. 2). A related example of a PPG signal for which there is a period of decreased signal quality will be shown in FIG. 9.

Plot 500 may contain several characteristics that may be used either individually or in combination to identify a period of decreasing signal quality. Plot 500 is comprised of time periods 520, 530, and 540. Time period 520 may correspond to a time period before a period of decreasing signal quality or it may correspond to a period in which a decreasing signal quality is largely imperceptible in PPG signal 510. In time period 520, PPG signal 510 has a relatively small light intensity amplitude and exhibits relatively large oscillations in the light intensity amplitude. A small light intensity amplitude may mean that a reduced amount of light is measured at detector 18 (FIG. 1), which may indicate that the target stimulus is being properly measured. Similarly, large oscillations in the amplitude may indicate the presence of strong pulse signal from patient 40 (FIG. 2), which may also indicate that the target stimulus is being properly measured.

In time period 530, PPG signal 510 exhibits a generally increasing light intensity amplitude and smaller oscillations in the light intensity amplitude compared to those exhibited in time period 520. These features may indicate that the signal quality of PPG signal 510 is decreasing. Such a decreasing trend in the signal quality of PPG signal 510 may be caused by any of a variety of factors, such as those discussed above. In addition to the these general trends, PPG signal 510 may exhibit scattered spurious effects that are characterized by rapid, and possibly temporary, changes in the light intensity amplitude. Examples include amplitude increase 550 and/or amplitude fluctuation 560. Amplitude increase 550 may correspond to, for example, a rapid and partial loosening of the pulse oximeter probe on patient 40 which causes more light to reach detector 18 (FIG. 1) from emitter 16 (FIG. 1). Amplitude fluctuation 560 may correspond to, for example, a temporary tightening and then re-loosening of the pulse oximeter probe on the target stimulus on patient 40 (FIG. 2), which temporarily decreases the amount of light received by detector 18 (FIG. 1).

Time period 540 may correspond to, for example, the case where the pulse oximeter probe is nearly or completely removed from the target stimulus on patent 40 (FIG. 2). In time period 540, PPG signal 510 reaches an approximately constant light intensity amplitude value 506. Also, PPG signal 510 exhibits only small oscillations in light intensity amplitude during this period. These characteristics may indicate that the intended target stimulus on patient 40 (FIG. 2) is no longer being measured to a significant degree.

As mentioned above, plot 500 was generated during an experiment in which the pulse oximeter probe was gradually loosened from the finger of patient 40 (FIG. 2) over time. However, as emphasized above, plot 500 is merely illustrative of a general PPG signal that may be obtained from, for example, pulse oximetry system 10 (FIG. 1) or system 400 (FIG. 4). Further, and as emphasized above, the target stimulus need not correspond to a patient finger, as many other target stimuli would produce a plot similar to plot 500. The actual rate of light intensity amplitude decrease may be faster or more gradual than that shown in time period 530, and the nature and number of energy increases and energy fluctuations in PPG signal 510 may be unpredictable and variable during time period 520.

Figure 6:
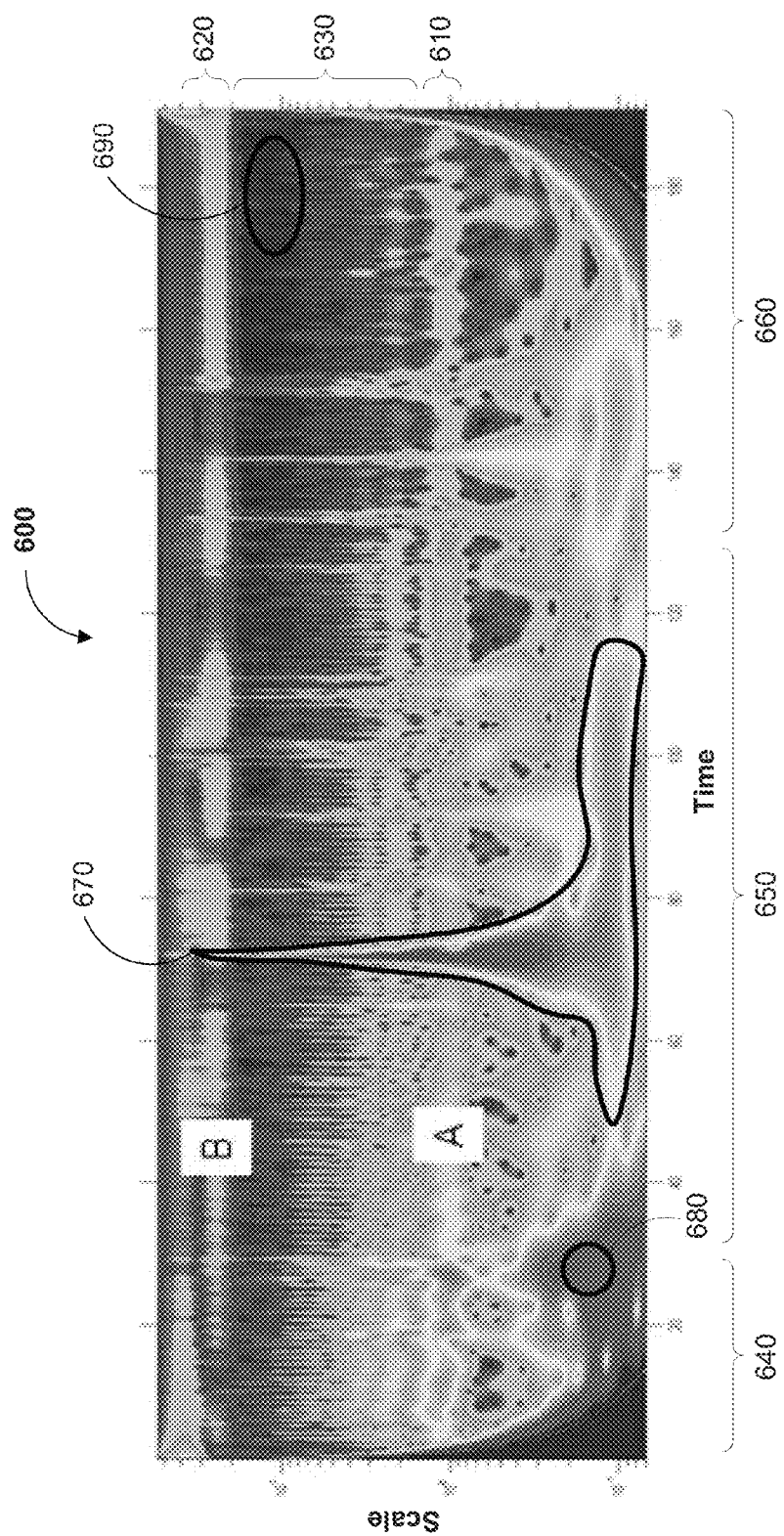
FIG. 6 shows an illustrative scalogram derived from the PPG signal of FIG. 5 in accordance with an embodiment.

FIG. 6 shows an illustrative scalogram 600 of a wavelet transform derived from a PPG signal such as PPG signal 510 (FIG. 5) during a period of decreasing signal quality in accordance with an embodiment. In scalogram 600, the x-axis of denotes time and the y-axis denotes scale. In scalogram 600, "hotter" colors (e.g., hues of red, orange and yellow) correspond to larger energy values, while "cooler" colors (e.g., hues of blue and green) correspond to smaller energy values. Dark red, which is the color of region 680, represents the largest energy value in scalogram 600, whereas dark blue, which is the color of region 690, represents the smallest energy values in scalogram 600. The regions in the lower left and lower right corners of the plot may contain energy values that reflect edge effects of the wavelet transform. These regions may be of a very high energy, and in scalogram 600 these regions have been replaced by energy values corresponding to the lowest energy values present in scalogram 600. This has been done so that energy values in these regions do not adversely influence the calculation of color scale used to generate scalogram 600. These regions may be ignored in the analysis of the scalogram.

Scalogram 600 comprises at least three distinct scale bands (i.e., ranges of scale values): pulse band 610, mains hum band 620, and noise band 630. Pulse band 610 may contain an energy structure and energy values that reflect the pulse component of PPG signal 510 (FIG. 5). When a pulse component is present in PPG signal 510 (FIG. 5) (e.g., when an accurate measurement of a target stimulus is made), pulse band 610 may be characterized by moderate to high energy values within the band and areas of lower energy at surrounding scale values. When a pulse component is not present in PPG signal 510 (FIG. 5) (e.g., when an accurate measurement of the target stimulus is not made), it may be expected that pulse band 610 will contain less energy. Mains hum band 620 may contain an energy structure and energy values that reflect the electrical or power line hum that is often characteristic of electric devices. The scales range that defines the mains hum band 620 may depend on characteristics of the alternating current supply (e.g., as used by pulse oximetry system 10 (FIG. 1)). When such a mains hum component is present in PPG signal 510 (FIG. 5), mains hum band 610 may be characterized by regular and rapidly oscillating streaks of low to moderate energy and areas of lower energy at surrounding scales. Noise band 630 may contain an energy structure and energy values that reflect general types of noise that may be present in PPG signal 510 (FIG. 5). For example, noise band 630 may be include the effects of thermal noise, shot noise, flicker noise, burst noise, and/or electrical noise caused by light pollution. Noise band 610 may be characterized as having less energy structure than either pulse band 610 or mains hum band 620, and as containing low-to-moderate energy values.

In scalogram 600, time periods 640, 650, and 660 correspond to the time periods 520, 530, and 540, respectively, as discussed in FIG. 5. Therefore, time period 640 corresponds to the time period for which the effect of the target stimulus is nearly or fully captured in the measurement of PPG signal 510 (FIG. 5). Time period 630 corresponds to a time period of decreasing signal quality, and time period 660 corresponds to the time period after which the effect of the target stimulus is largely or completely uncaptured in measurement of PPG signal 510 (FIG. 5). Within pulse band 610, energy values are seen to be moderate in time period 640, decreasing from moderate to low in time period 650, and low in time period 660. This may reflect the diminishing presence of a measurable pulse component signal in PPG signal 510 (FIG. 5) during time period 650. In contrast, the energy in the mains hum band 620 remains approximately constant throughout time periods 640, 650, and 660. This is because the mains hum noise is generated by electrical circuitry and may not depend on the signal that is measured (e.g., by detector 18 (FIG. 1)). The energy in noise band 630 decreases from moderate and low energy values in time period 640 to very low energy values in time period 660. This is because certain components of PPG signal 510 (FIG. 5) are contained within the scales comprising the noise band 630. Therefore, as the quality of the PPG signal 510 (FIG. 5) decreases, these components are not measured by, for example, detector 18 (FIG. 1), which results in less energy being detected in noise band 630.

Broadscale high-energy cone 670 is a sporadic effect caused by energy fluctuation 560 (FIG. 5) and is characterized by a cone-shaped region of high-energy that has a width that decreases as the scale value increases. The location and number of broadscale high-energy cones is in general variable and may be unpredictable in advance. However, the presence of one or more broadscale high-energy cones in a time period such as time period 650 may be indicative a signal quality decrease in that time period.

Figure 7:
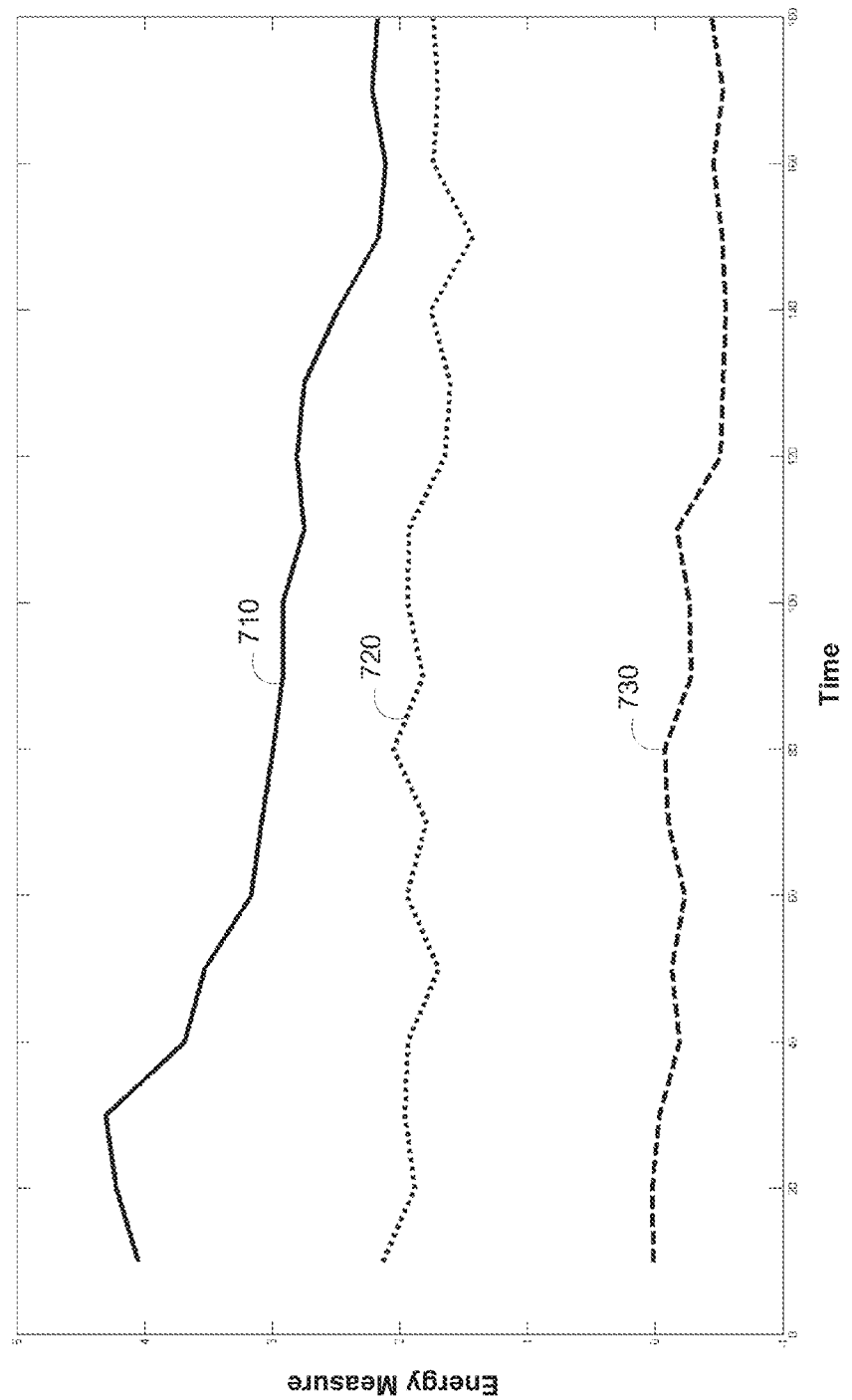
FIG. 7 shows illustrative plots of an energy measure versus time derived from the scalogram of FIG. 6 in accordance with an embodiment.

FIG. 7 shows illustrative plots of an energy measure versus time derived from scalogram 600 (FIG. 6). Each plot in FIG. 7 has been calculated by taking the tenth-percentile of the energy density values in scalogram 600 (FIG. 6) over a 10-second long time-window that includes a certain range of scale values. For example, plot 710 has been generated by selecting scale values in pulse band 610 (FIG. 6), plot 720 has been generated by selecting scale values in the mains hum band 620 (FIG. 6), and plot 730 has been generated by selecting scale values in the noise band 630 (FIG. 6). The energy measure plotted in FIG. 7 has been plotted using a logarithmic scale on the y-axis. It should be noted that plot 710 has the largest amplitudes followed by plot 720 and then plot 730. This is expected because, as discussed in relation to scalogram 600 (FIG. 6), pulse band 610 (FIG. 6) has the largest energy, followed by mains hum band 620 (FIG. 6) and noise band 630 (FIG. 6). Plot 710 exhibits a decrease in the energy measure in the pulse band versus time (e.g., plot 710 has a value of approximately 4 at time 10, and decreases to a value of approximately 2.25 at time 180) and plot 720 shows a relatively constant energy value in time (e.g., plot 720 has a value of approximately 2.1 at time 10, and a value of approximately 1.9 at time 180). These results are expected because, as discussed in relation to scalogram 600 (FIG. 6), pulse band 610 (FIG. 6) decreases in energy versus time, while mains hum band 620 (FIG. 6) has an approximately constant energy versus time. Plot 730 shows a small to moderate energy decrease in energy versus time (e.g., plot 730 has a value of approximately 0 at time 10, and a value of approximately −0.6 at time 180). In general, the level of decrease in plot 730 depends, at least in part, on the percentile threshold chosen in to generate plot 730. The energy used above is merely illustrative. Alternative energy measures (i.e., other than taking the tenth-percentile value in the window) can be employed. For example, summing all of the values of the lowest tenth-percentile may also be used.

In one embodiment, plots 710, 720, and/or 730 may be monitored and/or combined, and used to determine when and if a signal quality decrease has occurred or if one may occur. For example, plots 710, 720, and 730 may be parameterized through, for example, curve fitting using a linear straight line fit or a nonlinear curve fit. Alternatively, or in combination, plots 710, 720, and 730 may be combined through any suitable operation that, for example, weighs the values present in each plot or in some subset of plots. This weighted data may be compared to a threshold to determine if a signal quality decrease has occurred. Further, many changes to the parameters and features used to generate plots such as the ones illustrated in FIG. 7 may be made in accordance with an embodiment. For example, in choosing regions of the scalogram 600 (FIG. 6) over which to sum the energy density, the length of the time-window may be shortened or lengthened and may be chosen to include non-continuous segments; the selection of scale values used to compute each plot may be altered (e.g., to use more or fewer scale values); and/or a different threshold percentile (i.e., other than 10-percent) may be chosen in computing plot 730. Alternatively, instead of computing the tenth-percentile of energy density, plots may be generated by another energy measure. For example, plots may be generated in which the energy measure computes the lowest fifth-percentile, twentieth-percentile, or any other suitable percentile of energy values. Further, other properties of the wavelet transform can be use to generate plots other than or in addition to those of 710, 720, and 730. For example, the real and/or imaginary components, and various powers of the modulus and phase may be used.

Figure 8:
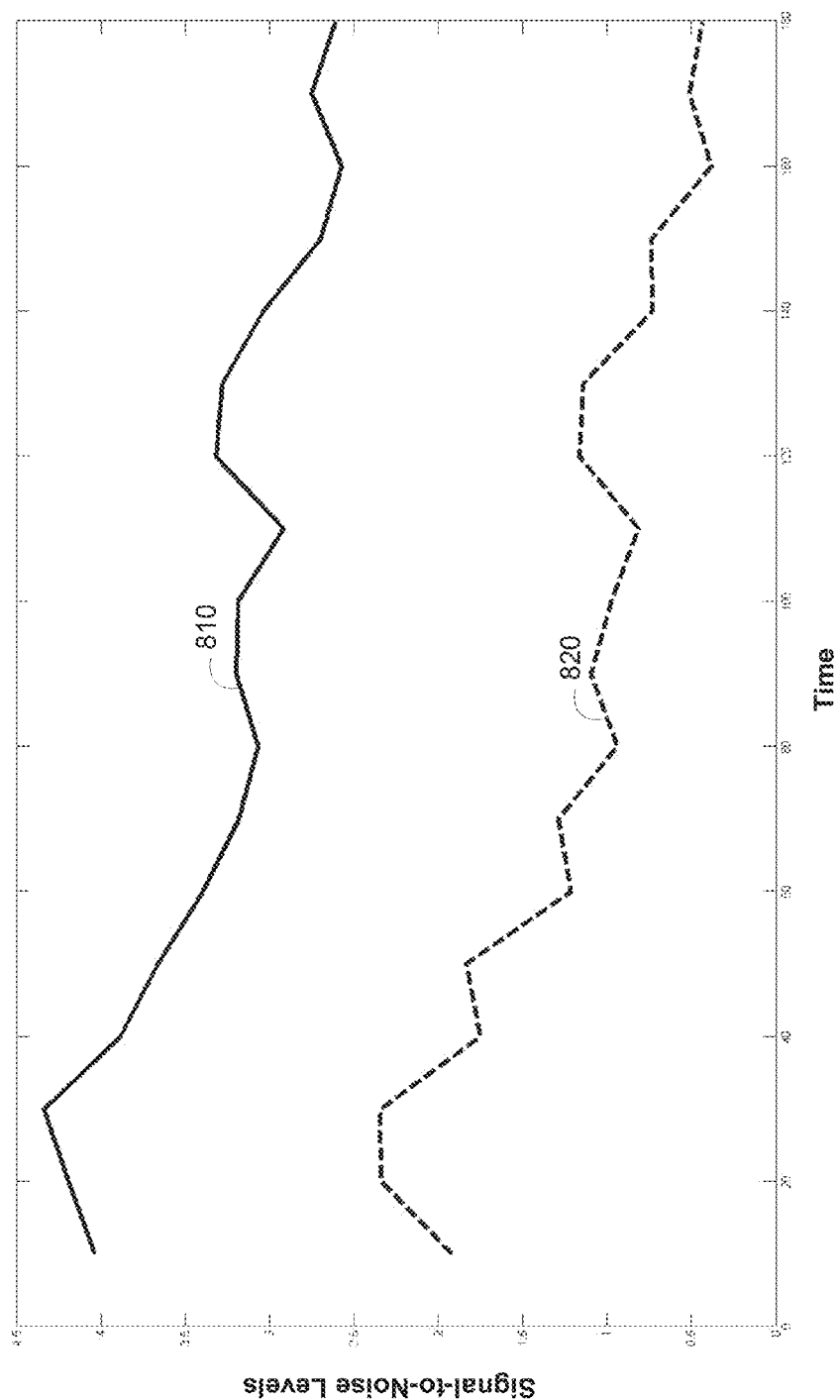
FIG. 8 shows illustrative plots of the signal-to-noise level versus time derived from FIG. 7 in accordance with an embodiment.

FIG. 8 shows illustrative plots of signal-to-noise levels versus time derived from FIG. 7. Plots 810 and 820 represent an illustrative technique for weighing the information in plots 710, 720, and 730 from FIG. 7 in accordance with an embodiment. Plot 810 is plot of the ratio of pulse band 610 (FIG. 6)

energy to the noise band 620 (FIG. 6) energy and is obtained by dividing, at each point in time, the value of plot 710 (FIG. 7) by the value of plot 730 (FIG. 7). Plot 820 is a plot of the ratio of the pulse band 610 (FIG. 6) energy to the mains hum band 620 (FIG. 6) energy and is obtained by dividing, at each point in time, the value of plot 710 (FIG. 7) by the value of plot 720 (FIG. 7). Signal-to-noise level plots such as 810 and 820 may be useful at least because they provide a measure of how the signal energy changes relative to a background noise level. For example, a large decrease in the signal energy might be tolerable, and not indicative of a signal quality decrease, if accompanied by a correspondingly large decrease in the noise level. In one embodiment, plots 810 and/or 820 may be combined and used to determine when a signal quality decrease occurs. For example, plots 810 and 820 may be combined through any suitable operation that weighs the values present in each plot to generate a new plot, which may be used to determine if a signal quality decrease has occurred. Plots 810 and 820 each have a signal decrease of roughly 1.5 from time 10 to time 180. In one embodiment, a signal quality decrease may be detected by comparing the average decrease from time 10 to time 180 between plots 810 and 820 to a threshold. If the average decrease exceeds this threshold value, then a signal quality decrease may be said to occur. The threshold may be calculated using any suitable technique. In one embodiment, such a threshold may be determined using statistical techniques such Neyman-Pearson hypothesis testing or the maximum-likelihood detection. Alternatively, such a threshold may be determined using historical data on signal-to-noise levels calculated before and during a signal quality decrease event. Alternatively or in combination, plots 810 and 820 may be parameterized through, for example, curve fitting using a linear straight line fit or a nonlinear curve fit before being used to determine whether a signal quality decrease has occurred.

Figure 9:
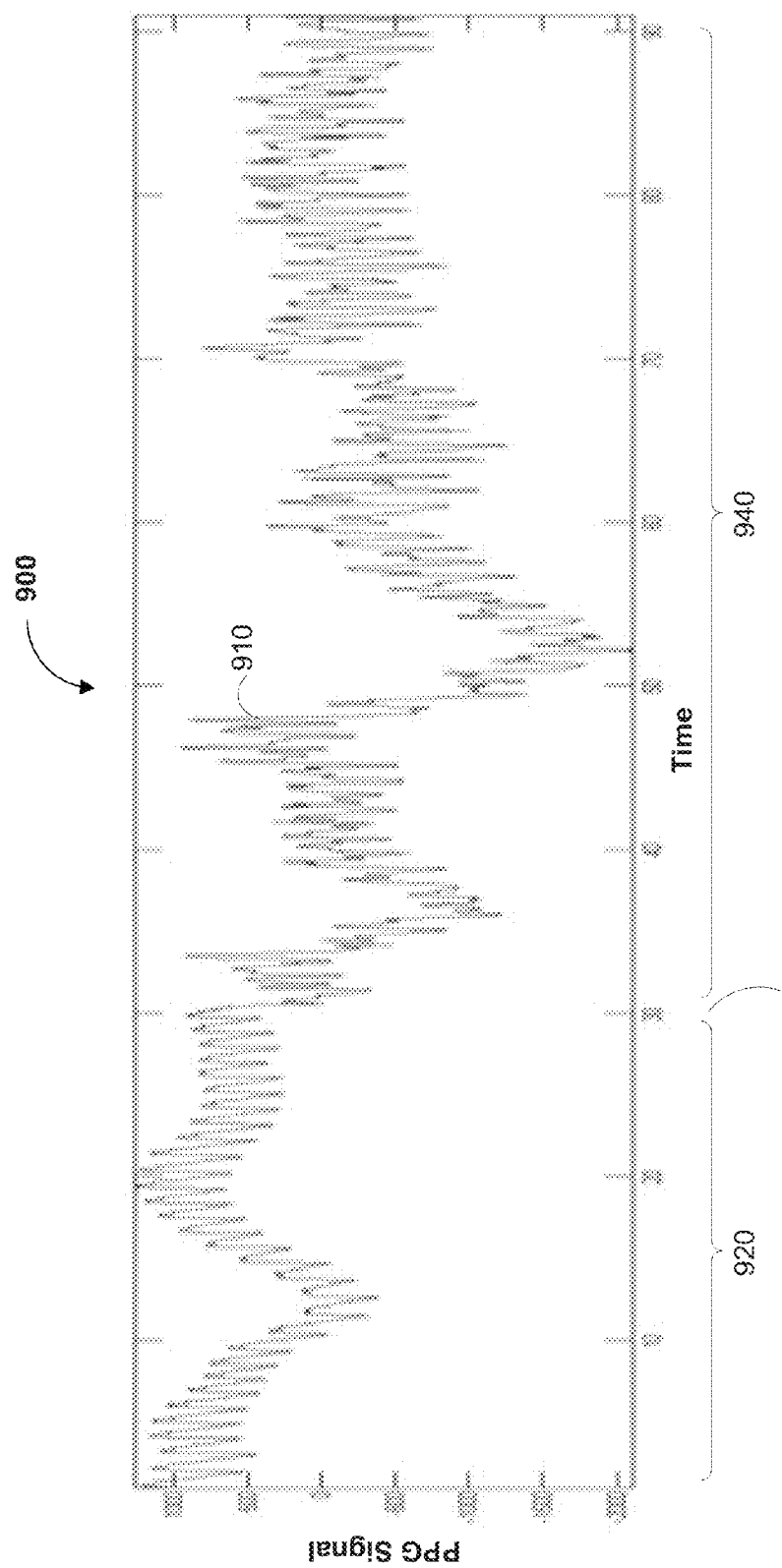
FIG. 9 shows an illustrative plot of a PPG signal taken prior to and during a period which includes a motion artifact in accordance with an embodiment.

FIG. 9 shows an illustrative plot of a PPG signal 910 taken prior to and during a period which includes a motion artifact in accordance an embodiment. As will be explained below, the occurrence of a motion artifact may result in a signal quality decrease in PPG signal 910. The definitions and meanings of the x-axis and y-axis in plot 900 are the same as for plot 500 (FIG. 5).

Plot 900 includes time periods 920 and 930. Time period 920 corresponds to a time period before a time period in which a motion artifact is present in PPG signal 910. Starting at approximately time 930, a significant motion artifact is measured in PPG signal 910. Such a motion artifact may be caused by, for example, voluntary or involuntary respiration, eye movements, swallowing, yawning, cardiac motion, and/or general body movement of patient 40. At approximately time 930, a motion artifact occurs in PPG signal 910. Time period 940 corresponds to a period in which a motion artifact remains present and measured by, for example, sensor 12. The presence of the motion artifact leads to a distinct change in PPG signal 910 during time period 940. The PPG signal exhibits larger and less smooth oscillations in light intensity amplitude during time period 940 than during time period 920. Further, the light intensity amplitudes exhibited in time period 940 are generally smaller than those exhibited in time period 920. These features may be used either singly or in combination to identify a period of decreased signal quality caused by a significant motion artifact or another related phenomena in PPG signal 910.

Figure 10:
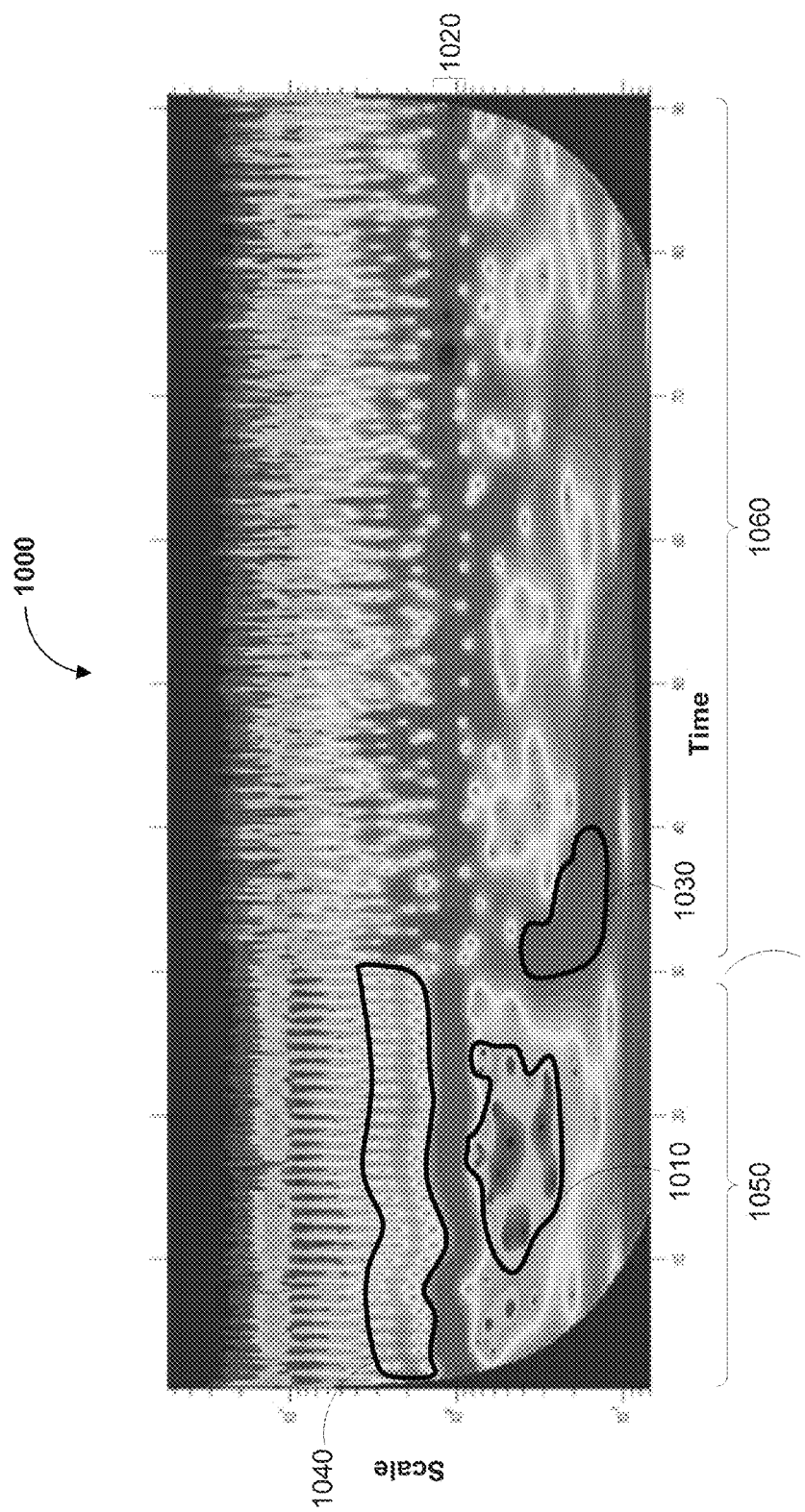
FIG. 10 shows an illustrative scalogram derived from the PPG signal of FIG. 9 in accordance with an embodiment.

FIG. 10 shows an illustrative scalogram derived from the PPG signal 910 (FIG. 9) in accordance with an embodiment. The axes values and the meanings of the colors in scalogram 1000 are the same as for scalogram 600 (FIG. 6). In scalogram 1000, region 1010 (having dark blue and light blue colors) and the lower-left and lower-right portions of the plot (each having a dark blue color) are the regions of the smallest energy, whereas scale band 1020 and region 1030 (having mostly dark red colors) are the regions of the largest energy, and region 1040 (having mostly yellow and orange colors) is a region of moderate energy. In scalogram 1000, time periods 1050 and 1060 correspond to the time periods 920 and 940, respectively, discussed above with respect to FIG. 9. Therefore, time period 1050 corresponds to a time period before the appearance and measurement of a motion artifact, and time period 1060 corresponds to period in which the motion artifact is present and measured. The motion artifact is first measured at time 1070 which corresponds to time 930 (FIG. 9). Scalogram 1000 exhibits different characteristics in time period 1050 than in time period 1060. The energy structure of scalogram 1000 is more random and the energy amplitudes of scalogram 1000 are larger in time period 1050 than in time period 1060. For example, the range of scales below scale band 1020 contain mostly low energy values in time period 1050 but mostly moderate and high energy values in time period 1060. The range of scales immediately above scale band 1020 contain structured and repeated energy characteristics in time period 1050 but relatively less well-defined energy characteristics in time period 1060. These features can be used to detect the presence of a signal quality decrease due to a motion artifact or other related phenomena.

Figure 11:
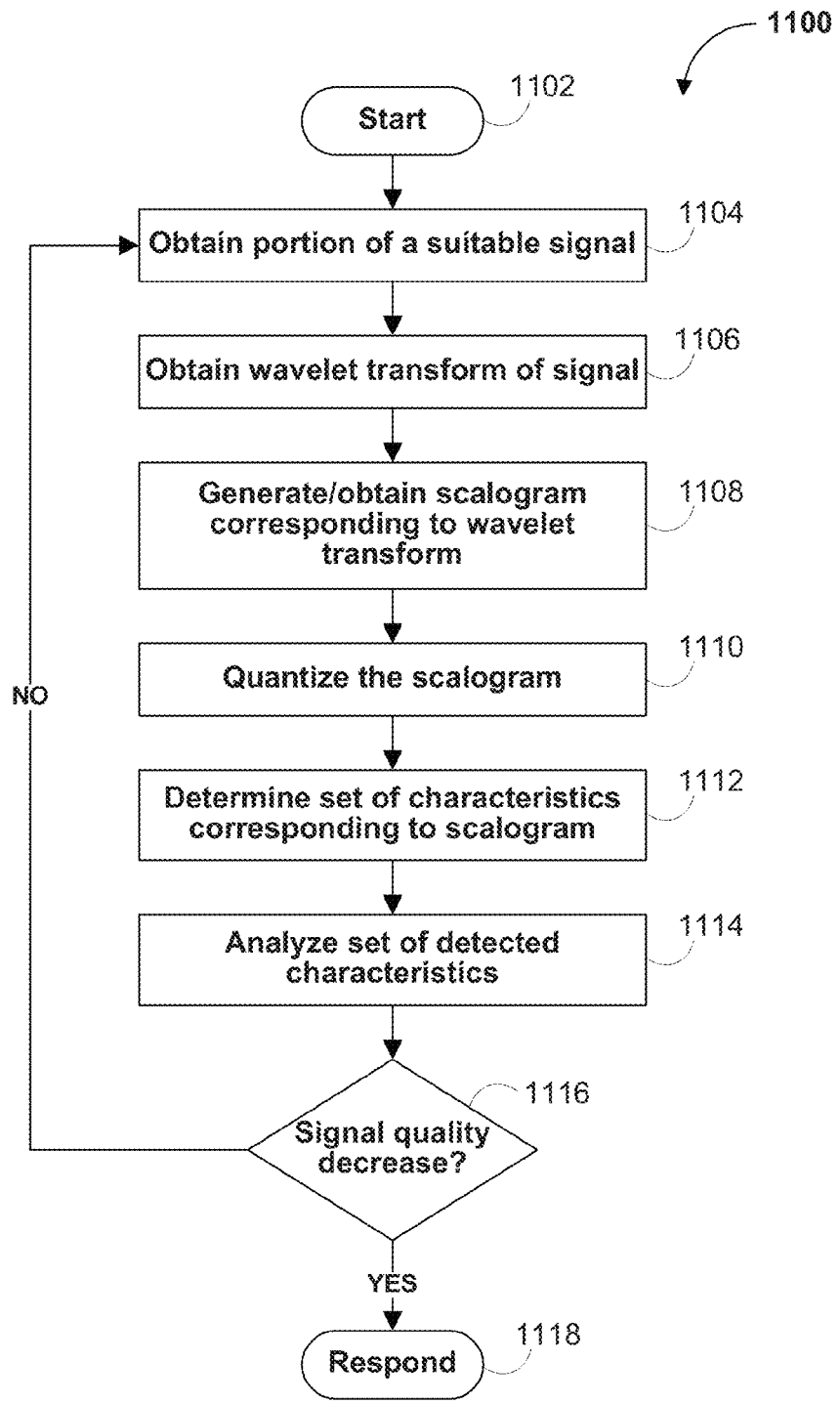
FIG. 11 is a flow chart of an illustrative process for determining and responding to a decrease in signal quality in accordance with an embodiment.

FIG. 11 is a flow chart 1100 of illustrative steps for determining and responding to a decrease in signal quality in accordance with an embodiment. Flow chart 1100 may begin at step 1102. At step 1104, a portion of a suitable signal may be obtained using, for example, pulse oximetry system 10 (FIGS. 1 and 2) or system 400 (FIG. 4). The signal may be obtained from a target stimulus provided by patient 40 (FIG. 2). The signal obtained may be a PPG signal. At step 1106, the wavelet transform of the signal may be obtained. Such a wavelet transform may be obtained, for example, by system 10 (FIGS. 1 and 2) or system 400 (FIG. 4). At step 1108, the scalogram of the wavelet transform may be generated or otherwise obtained using, for example a processor. For example, the scalogram of the wavelet transform may be generated or obtained using a processor such as processor 412 (FIG. 4) or microprocessor 48 (FIG. 2).

In addition to the scalogram, other parts of the wavelet transform may be inspected to determine whether a signal quality decrease event has occurred. For example, the transform modulus, phase, real, and/or imaginary parts may be generated at step 1108 in place of or in addition to the scalogram. Each of these features may then be used, either individually or in combination, in the subsequent steps of flow chart 1100. For example, the transform modulus or real, and/or imaginary values corresponding to the wavelet transform may be summed or otherwise manipulated to generate plots that can be used along with, or instead of, the plots shown in FIG. 7 and FIG. 8 to determine whether a signal quality decrease event has occurred. Alternatively or in addition to the method describe above, the phase of a wavelet transform may be analyzed across a range of scale values. The stability of phase values may indicate a relative value of the signal quality, and may be used to determine whether a signal quality decrease event has occurred.

Referring back to FIG. 11, at step 1110, the scalogram obtained in step 1108 may be quantized. Quantization refers to a process of truncating a continuous or (high-precision) digital signal value to a nearest reference value. The number of reference values may be significantly smaller than the number of values present in the signal prior to quantization.

Quantization may be beneficial at least for decreasing the complexity of hardware and software resources required to process and store the scalogram obtained in step 1108, as well as to further aid in the detection and analysis of features of the scalogram in subsequent steps 1112 and 1114. Quantization may provide these benefits with only a small or imperceptible degradation in the quality of the quantized signal relative to the quality of the signal prior to quantization. Any suitable quantization scheme may be used in step 1110. For example, quantization of the scalogram obtained in step 1108 may be performed using one, two, or multiple thresholds, whereby the quantized scalogram is obtained by rounding energy values of the original scalogram to the nearest threshold value. The threshold value may be calculated using any suitable technique. In one embodiment, such a threshold may be determined using statistical techniques such Neyman-Pearson hypothesis testing or the maximum-likelihood detection. Alternatively, such a threshold may be determined using historical data on signal-to-noise levels calculated before and during a signal quality decrease event. In addition, the number and value of quantization levels may be chosen based on the dynamic range of scalogram obtained in step 1108, the computational resources available, or based on a combination of these and any other suitable factors. Each threshold may be a variable quantity that varies with, for example, the time or scale value. It will be understood that step 1110, as well all other steps of flow chart 1100, is optional and that quantization of the scalogram need not be performed.

Referring back to FIG. 11, at step 1112, one or more characteristics of the scalogram obtained in step 1108 or 1110 may be determined using a processor. One or more of the characteristics that is determined may be chosen to be beneficial in determining if a signal quality decrease has occurred. For example, characteristics that may be determined include the energy and structure of the scalogram in pulse band 610 (FIG. 6), mains hum band 620 (FIG. 6), and/or noise band 630 (FIG. 6), and the signal-to-noise levels in various regions of scalogram 600 (FIG. 6). In one embodiment, this information may be calculated one or more times using different time-window sizes. The number and type of time-window sizes that are used may depend on the anticipated rate of a possible signal quality decrease, the available computational resources (e.g., the amount of ROM 52 (FIG. 2) and/or RAM 54 (FIG. 2) and the speed of processor 412 (FIG. 4) and/or microprocessor 48 (FIG. 2)), as well as on possible input derived from user inputs 56 (FIG. 2).

Referring back to FIG. 11, at step 1114, the characteristics determined in step 1112 may be analyzed. Analyzing the characteristics may generally involve parsing, combining, and/or weighing individual results obtained in the current and possible previous iterations of step 1114 so that a single, overall decision may be made as to whether a signal quality decrease has occurred. Step 1114 may incorporate the use of past scalogram data that has been obtained in previous iterations of process 1100 to determine current signal quality values and also trends in the signal quality values. For example, a signal quality value may be represented by a number from 0 to 100, where a larger number indicates a higher quality signal, and a trend may be represented by a number representing a rate increase or decrease in the signal quality. Past scalogram data may be stored in, for example, ROM 52 (FIG. 2) and/or RAM 54 (FIG. 2). Step 1114 may also involve the parameterization and/or curve fitting of data obtained in step 1112 using, for example, linear least-squares fitting of data or any other suitable interpolation technique. Such parameterization and/or curve fitting may be performed, for example, by processor 412 (FIG. 4) or microprocessor 48 (FIG. 2), and may additionally depend on parameters entered by a user through user inputs 56 (FIG. 2). In step 1114, multiple signal quality values and trend data may be combined to produce a simple form of data that may be used to make a single overall decision as to the possible presence of a signal quality decrease in a PPG signal such as PPG signal 510 (FIG. 5) or PPG signal 910 (FIG. 9). Any suitable parsing, combining, and/or weighing strategy may be used. For example, maximum-likelihood techniques may be used to combine data when the prior probability of a signal decrease event is known, and Neyman-Pearson combining techniques may be used when the prior probability of a signal quality decrease event is unknown. In addition, simply majority-vote decision rules may be used to determine if a signal quality decrease has occurred.

Referring back to FIG. 11, at step 1116, a decision may be made as to whether a decrease in signal quality has occurred. Such a decision may be made based on the output of step 1114. If it is determined that a decrease in signal quality has occurred, a response may be initiated in step 1118. A response may include many features singly or in combination. For example, possible features may include generating an audible alert or alarm that is emitted, for example, using speaker 22 (FIG. 2) as well as possibly through other audio devices, generating an on-screen message, for example, on display 20 (FIG. 1) or display 28 (FIG. 1), generating a pager message, a text message, or a telephone call, for example, using a wireless connection embedded or attached to a system such as system 10 (FIG. 1), activating a secondary or backup sensor or sensor array, for example, connected through a wire or wirelessly to monitor 14 (FIG. 1), or regulating the automatic administration medicine, for example, which is controlled in part or fully through a system such as system 10 (FIG. 1). If it is determined that a signal quality decrease has not occurred, then process 1100 returns to step 1104 and the "next" portion of the signal is obtained. The next portion of the signal may start where the previously read signal ended, overlap with the previously read signal, or be located at some distance in the future from the previously read signal. In any of these or in other scenarios, the choice of the signal region to be selected may be influenced by the data determined in step 1112 or analyzed in step 1114.

Figure 12:
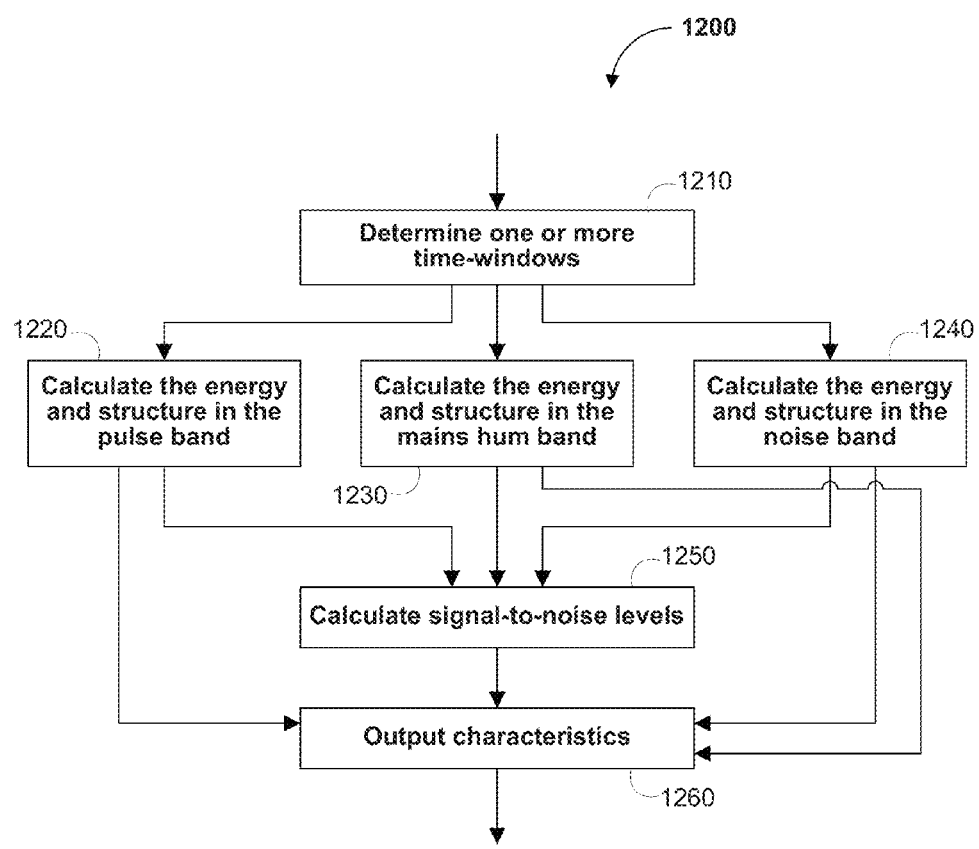
FIG. 12 shows a flow chart of an illustrative process for determining a set of characteristics in accordance with FIG. 11 and in an embodiment.

FIG. 12 shows a flow chart of illustrative steps for performing step 1112 of FIG. 11 (i.e., for determining a set of characteristics corresponding to a scalogram) in accordance with an embodiment. At step 1210, one or more time-windows may be determined and used to calculate the energy and other characteristics of the scalogram determined in step 1108 or step 1110. For example, and as described previously in relation to FIG. 7, the energy values and structural characteristics in the pulse band 610 (FIG. 6), mains hum band 620 (FIG. 6), and noise band 630 (FIG. 6) may be calculated. A separate time-window may be determined for each of these scale bands as well as other scale bands, and separate time-windows may be determined to measure energy values and energy structural characteristics. Time-windows may be of the same or different lengths, and each time-window may be comprised of either continuous or discontinuous ranges of time.

Referring back to FIG. 12, at step 1220, the energy values and energy structure in pulse band 610 (FIG. 6) may be calculated, for example, using one or more time-windows determined in step 1210. Energy values may be calculated by averaging the energy densities of a scalogram such as scalogram 600 (FIG. 6) within a given time-window as described in relation to FIG. 7, or through any other suitable technique. For example, energy may be calculated by averaging the energy density only over those energy values below a certain percentile threshold in pulse band 610 (FIG. 6), or by averaging only the minimum or maximum values at each time instant. Alternatively, the energy structure in pulse band 610 (FIG. 6) may be calculated by recording the presence of features within a given time-window such as the number of and frequency of repeated patterns, the presence of high energy regions followed by low energy regions, and/or any other suitable characteristics.

Referring back to FIG. 12, at step 1230, the energy values and energy structure in mains hum band 620 (FIG. 6) may be calculated, for example, using one or more time-windows determined in step 1210. Energy values may be calculated by averaging the energy densities of a scalogram such as scalogram 600 (FIG. 6) within a given time-window as described in relation to FIG. 7, or through any other suitable technique. For example, energy may be calculated by averaging the energy density only over energy values below a certain percentile threshold in mains hum band 620 (FIG. 6), or by averaging only the minimum or maximum values at each time instant. Alternatively, the energy structure in mains hum band 620 (FIG. 6) may be calculated by recording the presence of features within a given time-window such as the number of and frequency of repeated patterns, the presence of high energy regions followed by low energy regions, and/or any other suitable characteristics.

Referring back to FIG. 12, at step 1240, the energy values and energy structure in noise band 630 (FIG. 6) may be calculated, for example, using one or more time-windows determined in step 1210. Energy values may be calculated by averaging the energy densities of a scalogram such as scalogram 600 (FIG. 6) within a given time-window as described in relation to FIG. 7, and/or through any other suitable scheme. For example, energy may be calculated by averaging the energy density only over energy values below a certain percentile threshold in noise band 630 (FIG. 6), or by averaging only the minimum or maximum values at each time instant. Alternatively, the energy structure in noise band 630 (FIG. 6), may be calculated by recording the presence of features within a given time-window such as the number of and frequency of repeated patterns, the presence of high energy regions followed by low energy regions, and/or any other suitable characteristics.

Referring back to FIG. 12, at step 1250, signal-to-noise levels may be calculated corresponding to the characteristics determined in steps 1220, 1230, and 1240 above. One or more signal-to-noise levels may be calculated as described in relation to FIG. 8 or through any other suitable scheme. For example, the signal-to-noise level between the pulse band 610 (FIG. 6) and mains hum band 620 (FIG. 6) may be calculated by dividing, at each time point, the energy value obtained in step 1220 by the energy value obtained in step 1230. Alternatively, the signal-to-noise level between the pulse band 610 (FIG. 6) and noise band 630 (FIG. 6) may be calculated by dividing, at each time point, the energy value obtained in step 1220 by the energy value obtained in step 1240. At step 1260, the characteristics determined in steps 1220, 1230, 1240, and 1250 may be sent to step 1114 of process 1100 (FIG. 11).

Figure 13:
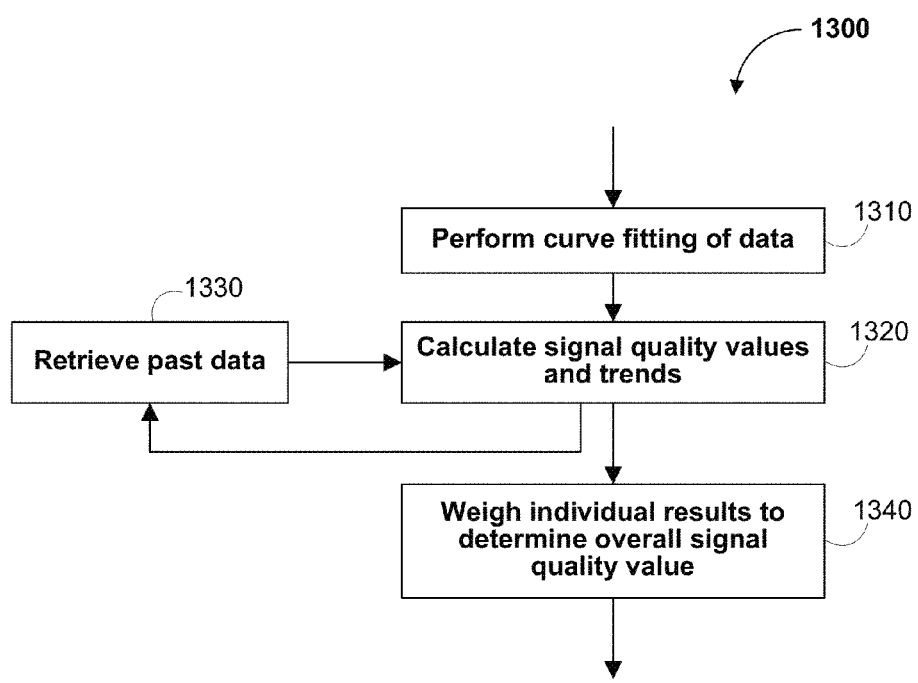
FIG. 13 shows a flow chart of an illustrative process for analyzing the set of characteristics in accordance with FIG. 11 and in an embodiment.

FIG. 13 is a flow chart of illustrative steps for performing step 1114 of FIG. 11, (i.e., analyzing the set of characteristics determined in step 1112) in accordance with an embodiment. At step 1310, curve fitting may be performed on the plots of energy values, energy structural characteristics, signal-to-noise levels, as well as on any other plots or other data types that may have been determined in step 1112. The curve fitting may be done using linear least-squares fitting of data, higher-order interpolative methods, or any other suitable technique. Parameterization and/or curve fitting can be performed, for example, by processor 412 (FIG. 4) or microprocessor 48 (FIG. 2), and may additionally depend on parameters entered by a user through user inputs 56 (FIG. 2). At step 1320, signal quality values and associated signal quality trends may be calculated based on current data obtained from step 1310 as well as from past data (generated in previous iterations of process 1100 (FIG. 11)) stored in step 1330. Such past data may be stored in, for example, ROM 52 (FIG. 2) and/or RAM 54 (FIG. 2). At step 1320, a separate signal quality value and related signal quality trend may be obtained for each type of available data. For example, a separate signal quality value and associated signal quality trend may be determined from each of the signal-to-noise level plots 810 (FIG. 8) and 820 (FIG. 8). A signal quality value may be represented by a number from 0 to 100, where a larger number indicates a higher quality signal and may be determined, for example, using tabulated figures or merit or through any other suitable scheme. In addition, signal quality trends may be determined and stored. A signal quality trend may be determined by comparing data obtained from step 1310 with past data obtained from step 1330. A trend may be characterized by a number representing a rate of increase or rate of decrease in the signal quality, or by another other suitable statistic. At step 1340, the multiple signal quality values and signal quality trends determined in step 1320 may be combined to produce a single signal quality value and associated signal quality trend. Any suitable parsing, combining, or weighing strategy may be used. For example, maximum-likelihood techniques may be used to combine data when the prior probability of a signal quality decrease event is known, and Neyman-Pearson combining techniques may be used when the prior probability of a signal quality decrease event is unknown. The overall signal quality value and associated signal quality trend may be passed to step 1116 (FIG. 11).

It will also be understood that the above method may be implemented using any human-readable or machine-readable instructions on any suitable system or apparatus, such as those described herein.

The foregoing is merely illustrative of the principles of this disclosure and various modifications can be made by those skilled in the art without departing from the scope and spirit of the disclosure. The following claims may also describe various aspects of this disclosure.

What is claimed is:

1. A method of determining signal quality information of a physiological signal, comprising:
   obtaining the physiological signal;
   generating a scalogram based at least in part on a wavelet transform of the physiological signal;
   determining one or more first characteristics of a pulse band of the scalogram;
   determining one or more second characteristics of a mains hum band or a noise band of the scalogram; and
   determining signal quality information of the physiological signal based at least in part on the one or more first characteristics and the one or more second characteristics.

2. The method of claim 1, wherein the one or more first characteristics comprise one or more of energy measures of the pulse band and energy structure of the pulse band.

3. The method of claim 1, wherein the one or more second characteristics comprise one or more of energy measures of the mains hum band, energy measures of the noise band, energy structure of the mains hum band, and energy structure of the noise band.

4. The method of claim 1, further comprising combining the one or more first characteristics and the one or more second characteristics.

5. The method of claim 4, wherein combining comprises dividing one of the one or more first characteristics and the one or more second characteristics by the other of the one or more first characteristics and the one or more second characteristics.

6. The method of claim 1, wherein determining the signal quality information comprises curve fitting the one or more first characteristics and the one or more second characteristics.

7. The method of claim 1, wherein determining the signal quality information comprises:
   determining one or more signal qualities based at least in part on the one or more first characteristics and the one or more second characteristics;
   determining one or more signal quality trends based on the one or more signal qualities; and
   determining an overall signal quality based on the one or more signal qualities and the one or more signal quality trends.

8. The method of claim 1, wherein determining the signal quality information comprises determining a signal quality decrease event.

9. The method of claim 1, wherein determining the signal quality information comprises determining a signal-to-noise level.

10. The method of claim 1, wherein the physiological signal is a photoplethysmograph signal.

11. A system for determining signal quality information of a physiological signal, comprising:
   a processor configured to:
      obtain the physiological signal;
      generate a scalogram based at least in part on a wavelet transform of the physiological signal;
      determine one or more first characteristics of a pulse band of the scalogram;
      determine one or more second characteristics of a mains hum band or a noise band of the scalogram; and
      determine signal quality information of the physiological signal based at least in part on the one or more first characteristics and the one or more second characteristics.

12. The system of claim 11, wherein the one or more first characteristics comprise one or more of energy measures of the pulse band and energy structure of the pulse band.

13. The system of claim 11, wherein the one or more second characteristics comprise one or more of energy measures of the mains hum band, energy measures of the noise band, energy structure of the mains hum band, and energy structure of the noise band.

14. The system of claim 11, wherein the processor is further configured to combine the one or more first characteristics and the one or more second characteristics.

15. The system of claim 14, wherein the processor is configured to combine the one or more first characteristics and the one or more second characteristics by dividing one of the one or more first characteristics and the one or more second characteristics by the other of the one or more first characteristics and the one or more second characteristics.

16. The system of claim 11, wherein the processor is configured to determine the signal quality information by curve fitting the one or more first characteristics and the one or more second characteristics.

17. The system of claim 11, wherein the processor is configured to determine the signal quality information by:
   determining one or more signal qualities based at least in part on the one or more first characteristics and the one or more second characteristics;
   determining one or more signal quality trends based on the one or more signal qualities; and
   determining an overall signal quality based on the one or more signal qualities and the one or more signal quality trends.

18. The system of claim 11, wherein the signal quality information comprises a signal quality decrease event.

19. The system of claim 11, wherein the signal quality information comprises a signal-to-noise level.

20. The system of claim 11, wherein the physiological signal is a photoplethysmograph signal.

* * * * *